United States Patent
Kang et al.

(10) Patent No.: US 11,054,427 B2
(45) Date of Patent: *Jul. 6, 2021

(54) METHOD OF QUANTIFYING BIOMARKER WITH HIGH SENSITIVITY USING PHOTO-OXIDATION INDUCED AMPLIFICATION

(71) Applicant: INTEKPLUS CO., LTD., Daejoen (KR)

(72) Inventors: Ji Yoon Kang, Seoul (KR); Min Cheol Park, Seoul (KR); Youhee Heo, Seoul (KR)

(73) Assignee: ABSOLOGY CO., LTD, Anyang-si (KR)

( * ) Notice: Subject to any disclaimer, the term of this patent is extended or adjusted under 35 U.S.C. 154(b) by 110 days.

This patent is subject to a terminal disclaimer.

(21) Appl. No.: 15/561,040

(22) PCT Filed: Mar. 21, 2017

(86) PCT No.: PCT/KR2017/003020
§ 371 (c)(1),
(2) Date: Sep. 23, 2017

(87) PCT Pub. No.: WO2017/171293
PCT Pub. Date: Oct. 5, 2017

(65) Prior Publication Data
US 2018/0180621 A1    Jun. 28, 2018

(30) Foreign Application Priority Data

Mar. 31, 2016    (KR) .................. 10-2016-0039414

(51) Int. Cl.
*G01N 33/58*    (2006.01)
(52) U.S. Cl.
CPC ....... *G01N 33/581* (2013.01); *G01N 2458/00* (2013.01)
(58) Field of Classification Search
CPC ............. G01N 2458/00; G01N 33/581; G01N 2333/90; G01N 33/53
See application file for complete search history.

(56) References Cited

U.S. PATENT DOCUMENTS

| | | | |
|---|---|---|---|
| 5,776,703 A * | 7/1998 | Bystryak ................. | C12Q 1/28 435/28 |
| 8,916,341 B1 * | 12/2014 | Bystryak .............. | G01N 33/542 435/4 |
| 8,951,722 B1 | 2/2015 | Bystryak et al. | |
| 2004/0116350 A1 * | 6/2004 | Wentworth, Jr. ...... | A61K 31/05 435/6.11 |
| 2011/0195858 A1 | 8/2011 | Selinfreund | |

FOREIGN PATENT DOCUMENTS

| | | |
|---|---|---|
| KR | 100237239 B1 | 6/1998 |
| KR | 1020150118107 A | 10/2015 |
| WO | WO2006016617 A1 | 7/2008 |

OTHER PUBLICATIONS

Cheow et al. Increasing sensitivity of enzyme-linked immunosorbent assay using multplexed electrokinetic concentrator. Anal. Chem., vol. 82, p. 3383-3388, 2010.*
Holenya et al., "KOMA: ELISA-microarray calibration and data analysis based on kinetic signal amplification," Journal of Immunological Methods, vol. 380, pp. 10-15. (Year: 2012).*
L.F. Cheow; Increasing the Sensitivity of Enzyme-Linked Immunosorbent Assay Using Multiplexed Electrokinetic Concentrator; Anal. Chem.; Apr. 15, 2010; 82, pp. 3383-3388; American Chemical Society; USA.
J. A. Kim; Magnetic beaddropletimmunoassayofoligomeramyloid β for the diagnosis ofAlzheimer's diseaseusingmicropillarstoenhancethe stability oftheoil—waterinterface; Biosensors andBioelectronics; Oct. 22, 2014; 67, 724-732; Elsevier; Netherland.
M. C. Park; Droplet-based magnetic bead immunoassay using microchannel-connected multiwell plates (μCHAMPs) for the detection of amyloid beta oligomers; Lab Chip; May 3, 2016; The Royal Society of Chemistry; UK.
M. Iranifam; Oscillating chemiluminescence systems: state of the art; Luminescence; Mar. 30, 2010; 25, 409-418; John Wiley & Sons, Ltd; USA.
International Search Report of PCT/KR2017/003020, dated Jun. 28, 2017, English Translation.
Semion M.Bystryak and Vladimr M.Mekler, Photochemical Amplification for Horseradish Peroxidase-Mediated Immunosorbent Assay, Institute of Chemical Physics, Sep. 16, 1991, vol. 202, pp. 390-393, Academic Press, Inc., Cambridge, USA.
Yusuke Obayashi et al, A single-molecule digital enzyme assay using alkaline phosphatase with a cumarin-based fluorogenic substrate, Royal Society of Chemistry, 2015, vol. 140, pp. 5065-5073, Royal Society of Chemistry, London, United Kingdom.
Baozhong Zhao et al, Photooxidation of Amplex red to resorufin; Implications of exposing the Amplex red assay to light, Free Radical Biology and Medicine, Jul. 3, 2012, vol. 53, pp. 1080-1087, Elsevier, Amsterdam, Netherlands.

(Continued)

*Primary Examiner* — Young J Kim
(74) *Attorney, Agent, or Firm* — STIP Law Group, LLC

(57) ABSTRACT

Disclosed is a method of quantifying a biomarker with high sensitivity using photo-oxidation induced amplification. The method includes performing an enzyme-substrate reaction of a measurement sample including an enzyme labeled on any one selected from among an antibody, an aptamer, and a nucleic acid specifically bound to the biomarker, optically measuring one or more optical properties selected from among amounts of color formation, light emission, and fluorescence of a product during a photo-oxidation induced amplification process while the product resulting from the enzyme-substrate reaction is continuously exposed to light to thus perform the photo-oxidation induced amplification process, indexing a time-varying pattern of the measured optical properties, and quantifying a concentration of the biomarker included in the measurement sample by comparing an index extracted during the indexing with an index of a reference sample.

8 Claims, 11 Drawing Sheets

(56) References Cited

OTHER PUBLICATIONS

Jun Deguchi et al, Photooxidation of Porphyrin in Mg-Substituted Horseradish Peroxidase, The journal of Biological Chemistry, Dec. 15, 1985, vol. 260, No. 29, pp. 15542-15546, The American Society of Biological Chemists, Inc, Rockville, USA.

Office Action from China Intellectual Property Administration of 201780003473.9, dated Aug. 7, 2019.

The extended European Search Report of EP17 77 5718, dated Oct. 11, 2019

Semion M. Bystryak et al, Photochemical Amplification for Horseradish Peroxidase-Mediated Immunosorbent Assay, Analytical Biochemistry, Sep. 16, 1991, pp. 390-393, vol. 202, Academic Press, Inc, Cambridge, USA.

Simon Bystryak et al, Increased Sensitivity of HIV-1 p24 ELISA Using a Photochemical Signal Amplification System, Basic and Translational Science, Oct. 1, 2015, pp. 109-114, Lippincott Williams & Wilkins, Philadelphia, USA.

Simon Bystryak and Rasa Santockyte, Increased Sensitivity of HIV-1 p24 ELISA Using a Photochemical Signal Amplification System, Journal of Acquired Immune Deficiency Syndrome , Oct. 1, 2015, pp. 109-114, vol. 70, No. 2, Lippincott, Philadelphia, USA.

\* cited by examiner

METHOD OF QUANTIFYING BIOMARKER WITH HIGH SENSITIVITY USING PHOTO-OXIDATION INDUCED AMPLIFICATION

CROSS-REFERENCE TO RELATED APPLICATIONS

This application is the U.S. National Phase under 35 U.S.C. § 371 of International Application No. PCT/KR2017/003020 filed on Mar. 21, 2017, which in turn claims the benefit of Korean Application No. 10-2016-0039414 filed on Mar. 31, 2016, the disclosures of which are incorporated by reference into the present application.

TECHNICAL FIELD

The present invention relates to a method of quantifying a biomarker with high sensitivity using photo-oxidation induced amplification. More particularly, the present invention relates to a method of quantifying a biomarker at a low concentration or in a small amount with high sensitivity using photo-oxidation induced amplification. In the method, a product resulting from a reaction of an enzyme, labeled on an antibody, an aptamer, or a nucleic acid, which is specific to the biomarker to be detected, with a substrate is continuously exposed to light, thus performing a photo-oxidation induced amplification process and indexing a time-varying pattern of amounts of color formation, light emission, and fluorescence of the product.

BACKGROUND ART

Generally, a method of detecting a biomarker such as a protein, a peptide, a gene, a hormone, or a low-molecular compound may be performed using an antibody, aptamer, or nucleic acid specific for the biomarker to be detected.

In addition, examples of a method of quantifying the concentration of a biomarker detected using biomarker-specific antibodies, aptamers, or nucleic acids may include an enzyme immunoassay method (ELISA; enzyme-linked immunosorbent assay or EIA; enzyme-linked immunoassay).

The enzyme immunoassay method is an immunoassay method using specific antigen-antibody or antigen-aptamer binding, and may be said to be a method of quantitatively measuring an antigen such as a protein, a peptide, a hormone, and a low-molecular compound. Usually, an antibody or an aptamer that is specific for an antigen is labeled with an enzyme, and the enzyme is reacted with a substrate to perform quantification. Accordingly, the amounts of color formation, light emission, and fluorescence of the product obtained by the reaction of the enzyme, which is labeled on the antibody or the aptamer, with the substrate are optically measured to thus quantify a biomarker. Generally, the extent of enzyme-substrate reaction of a measurement sample may be optically measured using a plate reader or a spectrometer, and may be compared to the measurement value of the extent of enzyme-substrate reaction of a reference sample, thereby quantifying the amount of the biomarker.

The enzyme immunoassay may also be used to detect a gene biomarker. That is, a nucleic acid that can be complementarily bound to the gene biomarker to be detected is labeled with an enzyme, and the enzyme is reacted with a substrate to perform quantification. Accordingly, the amounts of color formation, light emission, and fluorescence of the product obtained by the reaction of the enzyme, which is labeled on the nucleic acid, with the substrate may be optically measured, and may be compared with the measurement value of the extent of enzyme-substrate reaction of a reference sample, thereby quantifying the amount of the biomarker.

However, in a conventional enzyme immunoassay method, when the amount of the biomarker to be detected is small or when the concentration thereof is low, the amounts of color formation, light emission, and fluorescence of the product obtained by the reaction of an enzyme, which is labeled on an antibody, an aptamer, or a nucleic acid, with a substrate cannot be detected, and it is impossible to accurately quantify a biomarker using a very small detection amount even if it is possible to detect some amount thereof. For example, as shown in FIG. 1, when the amount of the enzyme labeled on the antibody is small or when the concentration thereof is low, since the amount of fluorescence of the product that can be detected after the enzyme-substrate reaction is very small, it is impossible to accurately quantify the antibody in a small amount or at a low concentration.

DISCLOSURE

Technical Problem

Accordingly, the present invention has been made keeping in mind the above problems occurring in the prior art, and an object of the present invention is to provide a method of quantifying a biomarker at a low concentration or in a small amount with high sensitivity using photo-oxidation induced amplification. In the method, a product resulting from reaction of an enzyme labeled on an antibody, an aptamer, or a nucleic acid, which is specific to the biomarker to be detected, with a substrate is continuously exposed to light, thus performing a photo-oxidation induced amplification process and indexing a time-varying pattern of amounts of color formation, light emission, and fluorescence of the product.

Technical Solution

In order to accomplish the above object, the present invention provides a method of quantifying a biomarker with high sensitivity using photo-oxidation induced amplification. The method includes performing an enzyme-substrate reaction of a measurement sample including an enzyme labeled on any one selected from among an antibody, an aptamer, and a nucleic acid, which are specifically bound to the biomarker, optically measuring one or more optical properties selected from among amounts of color formation, light emission, and fluorescence of a product during a photo-oxidation induced amplification process while the product resulting from the enzyme-substrate reaction is continuously exposed to light to thus perform the photo-oxidation induced amplification process, indexing a time-varying pattern of the measured optical properties, and quantifying a concentration of the biomarker included in the measurement sample by comparing an index extracted during the indexing to an index of a reference sample.

Advantageous Effects

According to the present invention having the above-described technical characteristics, a product resulting from reaction of an enzyme labeled on an antibody, an aptamer, or a nucleic acid, which is specific to a biomarker to be detected, with a substrate is continuously exposed to light, thus performing a photo-oxidation induced amplification process and indexing a time-varying pattern of amounts of color formation, light emission, and fluorescence of the product. Thereby, it is possible to more accurately quantify a biomarker present at a low concentration or in a small amount with high sensitivity.

BEST MODE

Unless defined otherwise, all technical and scientific terms used in this specification have the same meanings as would be generally understood by those skilled in the related art to which the present invention pertains. In general, the nomenclature used herein is well known and commonly used in the art.

In the specification, when any portion "includes" any component, this means that the portion does not exclude other components but may further include other components unless otherwise stated.

Hereinafter, embodiments of the present invention will be described in detail with reference to the accompanying drawings.

Figure 1:
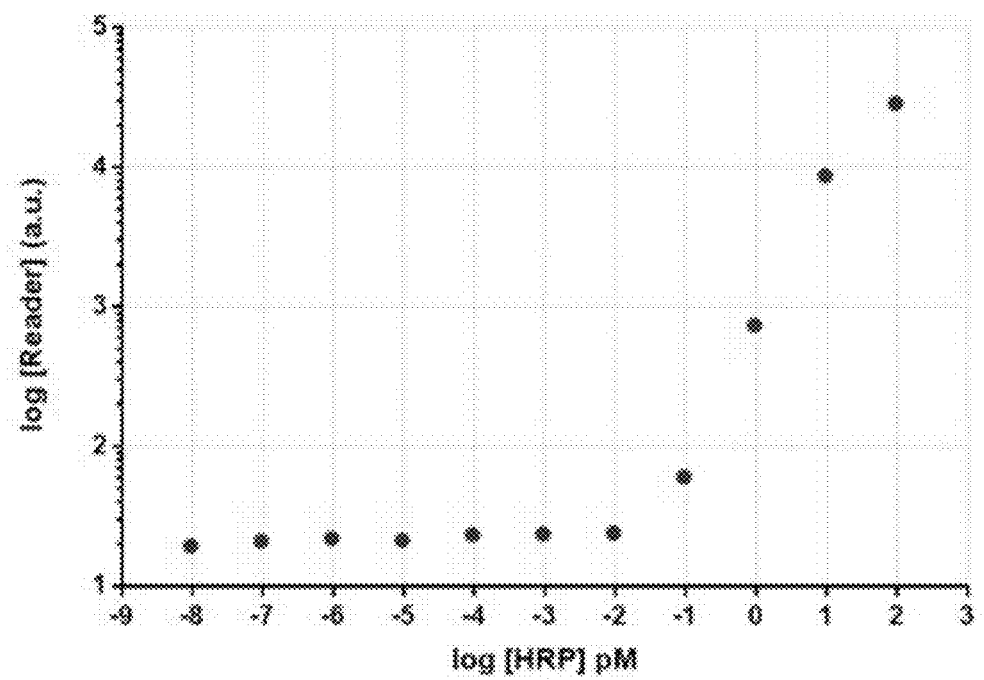
FIG. 1 is a graph showing the amount of fluorescence detection of an enzyme-substrate reaction product depending on the concentration of an enzyme using a plate reader of the prior art.
Figure 2:
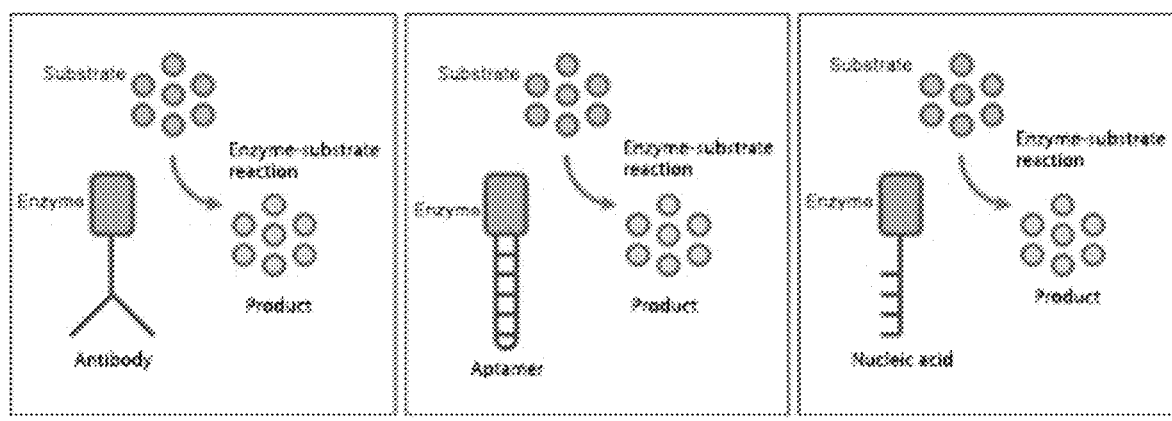
FIG. 2 is a conceptual diagram showing the reaction of an enzyme, which is labeled on an antibody, an aptamer, or a nucleic acid specifically bound to a biomarker according to an embodiment of the present invention, with a substrate.

FIG. 2 is a conceptual diagram showing the reaction of an enzyme, which is labeled on an antibody, an aptamer, or a nucleic acid specifically bound to a biomarker according to an embodiment of the present invention, with a substrate.

Referring to FIG. 2, the enzyme labeled on the antibody, the aptamer, or the nucleic acid specifically bound to the biomarker is converted into a product having colors or fluorescence due to reaction with the substrate. The amounts of color formation, light emission, and fluorescence of the product resulting from an enzyme-substrate reaction for a predetermined time may be optically measured to analyze the extent of the enzyme-substrate reaction. The extent of the enzyme-substrate reaction may be analyzed to thus analyze the amount of the enzyme labeled on the antibody, the aptamer, or the nucleic acid specifically bound to the biomarker, thereby quantifying the amount of the biomarker to be detected.

Figure 3:
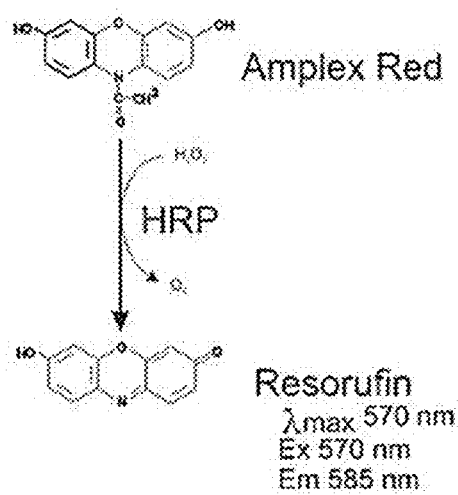
FIG. 3 is a view showing the reaction between an enzyme (HRP; horseradish peroxidase) and a substrate (Amplex Red) in an enzyme immunoassay method according to the embodiment of the present invention.

FIG. 3 is an example, and is a view showing the reaction between an enzyme (HRP; horseradish peroxidase) and a substrate (Amplex Red) in an enzyme immunoassay method according to the embodiment of the present invention.

Referring to FIG. 3, a colorless and non-fluorescent substrate (Amplex Red) is converted into a product (resorufin) having colors and fluorescence due to the action of an enzyme (HRP). The amount of fluorescence of the product may be measured using a plate reader to thus analyze the extent of enzyme-substrate reaction, whereby the amount of the enzyme labeled on the antibody, the aptamer, or the nucleic acid specifically bound to the biomarker, or the amount of the biomarker may be quantified. For example, an antibody specifically bound to an antigen may be labeled with an enzyme such as peroxidase and the extent of enzyme-substrate reaction may be measured, thereby quantifying the amount of the antigen to be detected.

However, in a conventional method of measuring an enzyme-substrate reaction using a plate reader or a spectrometer, when the amount of a biomarker included in a measurement sample is small or the concentration thereof is low, it is impossible to detect the amounts of color formation, light emission, and fluorescence of the product obtained due to reaction of an enzyme, which is labeled on an antibody, an aptamer, or a nucleic acid specific to a biomarker, with a substrate, and it is impossible to accurately quantify the biomarker using a very small detection amount even if it is possible to detect some amount thereof.

In order to solve this, in the present invention, the product resulting from the reaction of the enzyme, which is labeled on the antibody, the aptamer, or the nucleic acid specifically bound to the biomarker, with the substrate may be continuously exposed to light, thus amplifying the amount of color formation, light emission, and fluorescence of the product to a detectable amount using a photo-oxidation induced amplification process and indexing a variation pattern thereof, whereby it is possible to more accurately quantify a biomarker present at a low concentration or in a small amount with high sensitivity.

In order to quantify the biomarker to be detected using photo-oxidation induced amplification with high sensitivity, in the present invention, the measurement sample including the enzyme labeled on any one selected from among the antibody, the aptamer, or the nucleic acid which is specifically bound to the biomarker is first subjected to the enzyme-substrate reaction. The product resulting from the enzyme-substrate reaction is continuously exposed to light, whereby the photo-oxidation induced amplification process is performed, and one or more optical properties selected from among the amounts of color formation, light emission, and fluorescence of the product are optically measured during the photo-oxidation induced amplification process.

In the present invention, the biomarker may be any one selected from among a protein, a peptide, a gene, a hormone, and a low-molecular compound. Examples thereof may include a tumor (cancer) marker including AFP, CA 125, CA 15-3, CA 19-9, CA 72-4, calcitonin, CEA, Cyfra 21-1, hCG, HE4, NSE, proGRP, PSA, SCCA, STN, thyroglobulin, and TPA; a heart disease marker including troponin, myoglobin, and N-terminal proBNP; a degenerative brain disease marker including beta-amyloid, tau, alpha-synuclein, $PrP^{Sc}$, and huntingtin; an infectious disease marker including Anti-HAV, Anti-HBc, Anti-HBe, HBeAg, Anti-HBs, HBsAg, Anti-HCV, CMV IgG, CMV IgM, HIV, HIV-Ag, HSV-Ag, HSV-1 IgG, HSV-2 IgG, RSV IgG, RSV IgM, Rubella IgG, Rubella IgM, Syphilis, Toxo IgG, and Toxo IgM; an inflammatory disease marker including Anti-CCP, IgE, interleukin, procalcitonin, TNF, TGF, and VEGF; an endocrine disease marker including ACTH, Anti-Tg, Anti-TPO, Anti-TSH-R, calcitonin, cortisol, C-peptide, FT3, FY4, hGH, insulin, PTH STAT, T3, T4, thyreoglobulin, and TSH; autoimmune disease and allergic markers including Anti-$\beta$2-GP1 IgG/IgM, Anti Cardiolipin IgG/IgM, Anti ds-DNA Ab IgG/IgM, Anti GD1b IgG/IgM, Anti GM1 IgG/IgM, Anti GQ1b IgG/IgM, Anti Phospholipid IgG/IgM, Anti ss-DNA IgG/IgM, RA Factor IgG, various allergy-causing substances, and IgE; a bone metabolism marker including osteocalcin, P1NP, PTH, and Vitamin D; a drug test marker including Cyclosporine, Digitoxin, Sirolimus, and Tacrolimus; a pregnancy/prenatal check marker including hCG, FSH, HE4, progesterone, and testosterone; and a gene marker including Cytomegalovirus, Hepatitis B, Hepatitis C, Herpes, Influenza A/B, Chlamydia trachomatis, Mycobacteria Tuberculosis, HIV-2, HCV, HBV, Hepatitis E, Strep A, BRAF, KRAS, and EGFR. Further, biomarkers such as a tumor (cancer) marker, a heart disease marker, a degenerative brain disease marker, an infectious disease marker, an inflammatory disease marker, an endocrine disease marker, autoimmune disease and allergic markers, a bone metabolism marker, a drug test marker, a pregnancy/prenatal check marker, and a gene marker, which are not listed above, may be selected.

In the present invention, any one of the antibody, the aptamer, and the nucleic acid may be selected depending on the biomarker to be detected. When the enzyme labeled on the antibody, the aptamer, or the nucleic acid is reacted with the substrate, any one selected from among the antibody, the aptamer, and the nucleic acid is labeled with any one enzyme selected from among peroxidase including HRP (horseradish peroxidase), galactosidase including $\beta$-galactosidase, and phosphatase including AP (alkaline phosphatase). The measurement sample labeled with the enzyme is mixed with any one substrate selected from among ADHP (10-acetyl-3,7-dihydroxyphenoxazine; Amplex Red), RGP (resorufin-$\beta$-D-galactopyranoside), and MUP (4-methylumbelliferyl phosphate), thus performing the enzyme-substrate reaction for a predetermined time.

Further, when the enzyme-substrate reaction is performed, enzymes and substrates not listed above may be selected.

In the present invention, the optical properties selected from among the amounts of color formation, light emission, and fluorescence of the product of the enzyme-substrate reaction may be used separately or in combination depending on the enzyme that is labeled on the antibody, the aptamer, or the nucleic acid, or on the substrate that reacts with the enzyme.

In order to optically measure the optical properties, any one of white light having a broad wavelength, monochromatic light having a narrow wavelength, and a laser having a single wavelength may be selected as the light used for the photo-oxidation induced amplification. While the product of the enzyme-substrate reaction is continuously exposed to light, the optical properties of the product during the photo-oxidation induced amplification process may be continuously measured over time. Continuous or continued measurement of the optical properties may be performed by measuring video images using continuous exposure to light, by continuously measuring the optical properties in a short time interval, or by measuring the optical properties over time using intermittent exposure to light at a predetermined time interval.

Meanwhile, the time-varying pattern of the optical properties that are optically measured is indexed during the photo-oxidation induced amplification or until the amplification is finished.

In the present invention, 'indexing' refers to the extraction of indexes that accurately indicate measurement values of the optical properties over time, that is, the time-varying pattern of the measured optical properties, using various regression analyses.

Therefore, in the indexing of the present invention, various indexes of the time-varying pattern of the measured optical properties of the product may be extracted using regression analysis.

For example, one or more indexes, which are selected from the group including a regression analysis parameter of an optical property initial value, a regression analysis parameter of an optical property maximum value, a regression analysis parameter of a time required to reach half of the optical property maximum value, and a regression analysis parameter of an amplification ratio of the optical properties over time, may be extracted. That is, one or more may be selected from among the above-described indexes, and the selected indexes may be used separately or in various combinations.

The concentration of the biomarker included in the measurement sample may be quantified by comparing the index extracted during the indexing step with the index of the reference sample. Further, the index of the reference sample may be obtained from the photo-oxidation induced amplification pattern of the sample including the biomarker diluted at a predetermined concentration interval.

Figure 4:
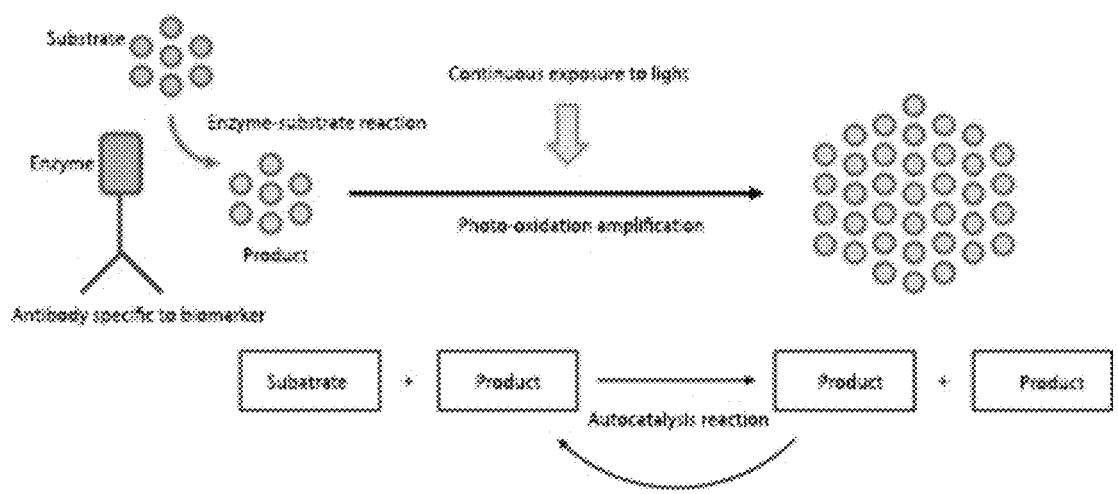
FIG. 4 is a conceptual diagram showing a photo-oxidation induced amplification process according to the embodiment of the present invention.

FIG. 4 is a conceptual diagram showing a photo-oxidation induced amplification process according to the embodiment of the present invention.

Referring to FIG. 4, the photo-oxidation induced amplification process occurs as a kind of autocatalysis reaction. That is, when the sample that is subjected to the enzyme-substrate reaction is continuously exposed to light, the amounts of color formation, light emission, and fluorescence of the product resulting from the enzyme-substrate reaction are amplified due to the autocatalysis reaction. Accordingly, the amounts of color formation, light emission, and fluorescence of the product may be measured for each photo-oxidation induced amplification time, thereby drawing the photo-oxidation induced amplification pattern.

Since the photo-oxidation induced amplification process is a kind of autocatalysis reaction, when the photo-oxidation induced amplification pattern is drawn over time, the pattern may be expressed by an S-shaped curve in a graph.

Further, during the enzyme-substrate reaction, different amounts of initial products are obtained depending on the concentration of the enzyme, and the rate of photo-oxidation induced amplification depends on the amount of the initial product that is obtained.

Accordingly, as the concentration of the enzyme labeled on the antibody, the aptamer, or the nucleic acid is increased, since the initial product is generated in a large amount, the rate of the autocatalysis reaction is high, and the photo-oxidation induced amplification is rapidly performed, thus rapidly amplifying the amount of fluorescence of the product. In contrast, as the concentration of the enzyme labeled on the antibody, the aptamer, or the nucleic acid is reduced, since the initial product is generated in a small amount, the rate of the autocatalysis reaction is low, and the photo-oxidation induced amplification is slowly performed, thus relatively slowly amplifying the amount of fluorescence of the product.

Therefore, the concentration of the enzyme labeled on the antibody, the aptamer, or the nucleic acid may be confirmed by comparing relative times required for amplification of the optical properties, such as the amounts of color formation, light emission, and fluorescence of the product. The photo-oxidation induced amplification pattern may be indexed over time, thus more accurately quantifying the concentration of the enzyme at a low concentration or in a small amount with high sensitivity.

As described above, the photo-oxidation induced amplification is caused by the autocatalysis reaction. Therefore, when the variation pattern of the optical properties, such as the amounts of color formation, light emission, and fluorescence of the product, according to the photo-oxidation induced amplification is drawn over time, the pattern may be expressed as an S-shaped curve. This can be understood by the reaction rate equation of the autocatalysis reaction shown in Equation 1 below.

$$AR + RSF \rightarrow RSF + RSF \qquad \text{[Equation 1]}$$
$$\frac{d[RSF]}{dt} = k[AR][RSF]$$

In Equation 1, AR represents Amplex Red (substrate), RSF represents resorufin (product), [AR] represents the concentration of AR, [RSF] represents the concentration of RSF, k represents the reaction rate constant or the amplification ratio of the autocatalysis reaction, and t represents the elapsed time of the autocatalysis reaction. An equation that represents the variation pattern of the RSF concentration depending on the elapsed time of the autocatalysis reaction may be derived as shown in the following Equation 2 by solving the reaction rate equation of the autocatalysis reaction of Equation 1.

$$[RSF] = \frac{[AR]_0 + [RSF]_0}{1 + \frac{[AR]_0}{[RSF]_0} e^{-([AR]_0 + [RSF]_0)kt}} \qquad \text{[Equation 2]}$$

In Equation 2, $[AR]_0$ represents the initial concentration of Amplex Red, and $[RSF]_0$ represents the initial concentration of resorufin. When the variation pattern of the amounts of color formation, light emission, and fluorescence of the product according to the photo-oxidation induced amplification is drawn over time, the pattern may be understood to be expressed by an S-shaped curve.

Therefore, the measurement value of the fluorescence amount of the product (resorufin) according to the elapsed time of the photo-oxidation induced amplification may be set as [RSF], and the regression analysis of the value of [RSF] over time (t) may be performed using Equation 2, thus deriving regression analysis parameters of $[AR]_0$, $[RSF]_0$, and k. The photo-oxidation induced amplification pattern may be indexed using the derived parameters.

Examples of the index of the photo-oxidation induced amplification pattern may include a regression analysis parameter of an initial value of the optical properties, such as the amounts of color formation, light emission, and fluorescence, of the product, a regression analysis parameter of an optical property maximum value of the product, a regression analysis parameter of the time required to reach half of the optical property maximum value of the product, and a regression analysis parameter of the amplification ratio of the optical properties of the product over time. One or more may be selected from among the parameters and may be used separately or in combination to calculate the index.

For example, when the regression analysis parameter of the time required to reach half of the maximum value of the amount of color formation, light emission, or fluorescence of the product is referred to as a $T_{50}$ index, the $T_{50}$ index may be derived as shown in Equation 3 below.

$$T_{50} = \frac{\ln\left(\frac{[AR]_0}{[RSF]_0}\right)}{([AR]_0 + [RSF]_0) \times k} \qquad \text{[Equation 3]}$$

As another example, when a CTL (characteristic time length) index indicates an index for combinedly calculating a regression analysis parameter of an initial value of the optical properties, such as the amounts of color formation, light emission, and fluorescence of the product, a regression analysis parameter of an optical property maximum value of the product, a regression analysis parameter of a time required to reach a half of the optical property maximum value of the product, and a regression analysis parameter of an amplification ratio of the optical properties of the product over time, the CTL index may be derived as shown in Equation 4 below.

$$CTL = T_{50} \times \text{Steepness}, \text{Steepness} = \frac{k}{(0.5 - [RSF]_0)/T_{50}} \qquad \text{[Equation 4]}$$

The index of the photo-oxidation induced amplification pattern may be extracted by performing regression analysis of the variation pattern of the amounts of color formation, light emission, and fluorescence of the product according to the photo-oxidation induced amplification using Equation 2.

The equation used for regression analysis may include other equations that are expressed by an S-shaped curve like Equation 2. Various indexes of the photo-oxidation induced amplification pattern may be derived depending on the equation used for regression analysis.

Mode for Invention

Example 1

In Example 1 of the present invention, photo-oxidation induced amplification patterns depending on the concentration of an enzyme are compared.

First, samples including various concentrations of enzymes are prepared, and an enzyme-substrate reaction is performed. The enzymes at various concentrations may include an enzyme labeled on an antibody, an enzyme labeled on an aptamer, and an enzyme labeled on a nucleic acid.

In Example 1 of the present invention, for example, a sample including no HRP enzyme (blank sample), a sample including the HRP enzyme labeled on the antibody, that is, HRP labeled on the antibody, and a 1×PBS buffer may be mixed to thus prepare various samples depending on the concentration. The samples may be mixed with an Amplex Red substrate, which causes an enzyme-substrate reaction for a predetermined time.

Next, the product (resorufin) resulting from the enzyme-substrate reaction of each sample is continuously exposed to light, thus performing a photo-oxidation induced amplification process. The amount of fluorescence of the product during the photo-oxidation induced amplification process is optically detected, and the time-varying pattern of the amount is indexed to compare the indexes of the photo-oxidation induced amplification pattern depending on the concentration of the enzyme labeled on the antibody.

Examples of the light used for photo-oxidation induced amplification may include a light having a broad wavelength such as a white light, a light having a narrow wavelength such as a monochromatic light, and a light having a single wavelength such as a laser. In Example 1 of the present invention, a green light in a wavelength band of 510 to 550 nm is used.

Figure 5:
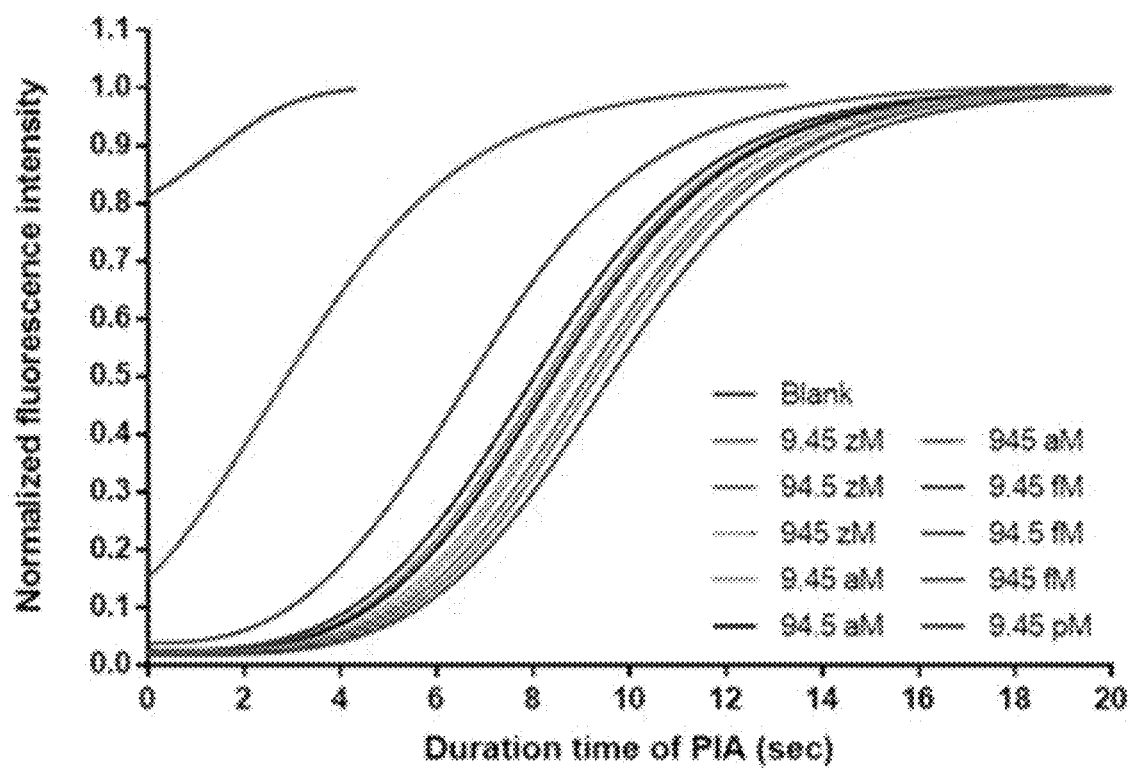
FIG. 5 is a graph showing a photo-oxidation induced amplification pattern over time, depending on the concentration of an enzyme labeled on an antibody according to Example 1 of the present invention.

FIG. 5 is a graph showing a photo-oxidation induced amplification pattern over time, depending on the concentration of an enzyme labeled on an antibody according to Example 1 of the present invention.

From FIG. 5, it can be confirmed that the photo-oxidation induced amplification pattern depends on the concentration of the enzyme labeled on the antibody. In other words, it can be confirmed that different amounts of the initial products are produced depending on the concentration of the enzyme during the enzyme-substrate reaction and that the photo-oxidation induced amplification rate depends on the amount of the initial product.

As a result, as the concentration of the enzyme bound to the antibody is increased, the amount of initial resorufin that is produced is increased. Accordingly, the rate of the autocatalysis reaction is increased and the photo-oxidation induced amplification is rapidly performed, resulting in a rapid change in fluorescence intensity value. In contrast, as the concentration of the enzyme bound to the antibody is reduced, the amount of initial resorufin that is produced is reduced. Accordingly, the rate of the autocatalysis reaction is reduced and the photo-oxidation induced amplification is slowly performed, resulting in a slow change in fluorescence intensity value.

Therefore, the concentration of the enzyme bound to the antibody may be confirmed by comparing relative times required for a change in fluorescence intensity value. When sampling is performed so that a difference in concentration of the samples is further increased, followed by storing, the enzyme-substrate reaction may be more accurately analyzed in detail using even a sample including the enzyme at a low concentration or in a small amount.

Figure 6:
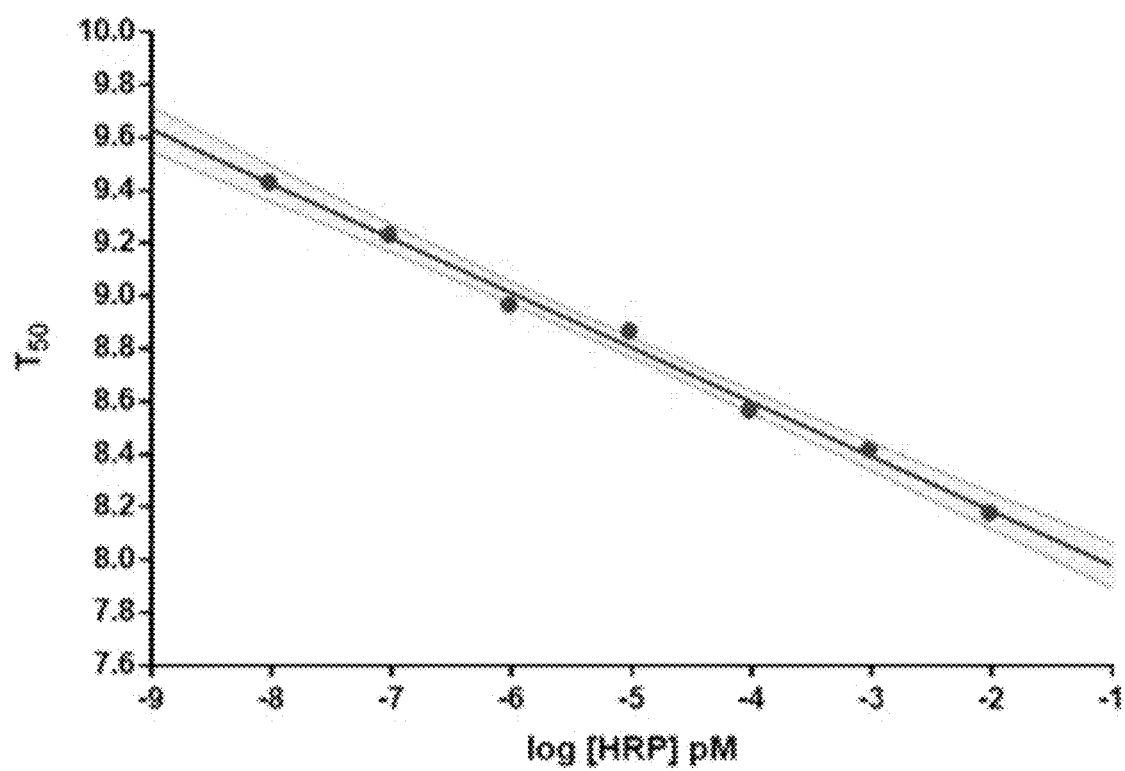
FIG. 6 is a graph showing $T_{50}$ index extraction values of the photo-oxidation induced amplification pattern depending on the concentration of the enzyme labeled on the antibody according to Example 1 of the present invention.

FIG. 6 is a graph showing $T_{50}$ index extraction values of the photo-oxidation induced amplification pattern depending on the concentration of the enzyme labeled on the antibody according to Example 1 of the present invention.

As can be seen in FIG. 6, as the concentration of the enzyme is reduced, a $T_{50}$ index indicating the time required to reach half of the maximum value of the amount of color formation, light emission, or fluorescence of the product is increased. Accordingly, the concentration of the enzyme at a low concentration or in a small amount may be more accurately quantified with high sensitivity.

Figure 7:
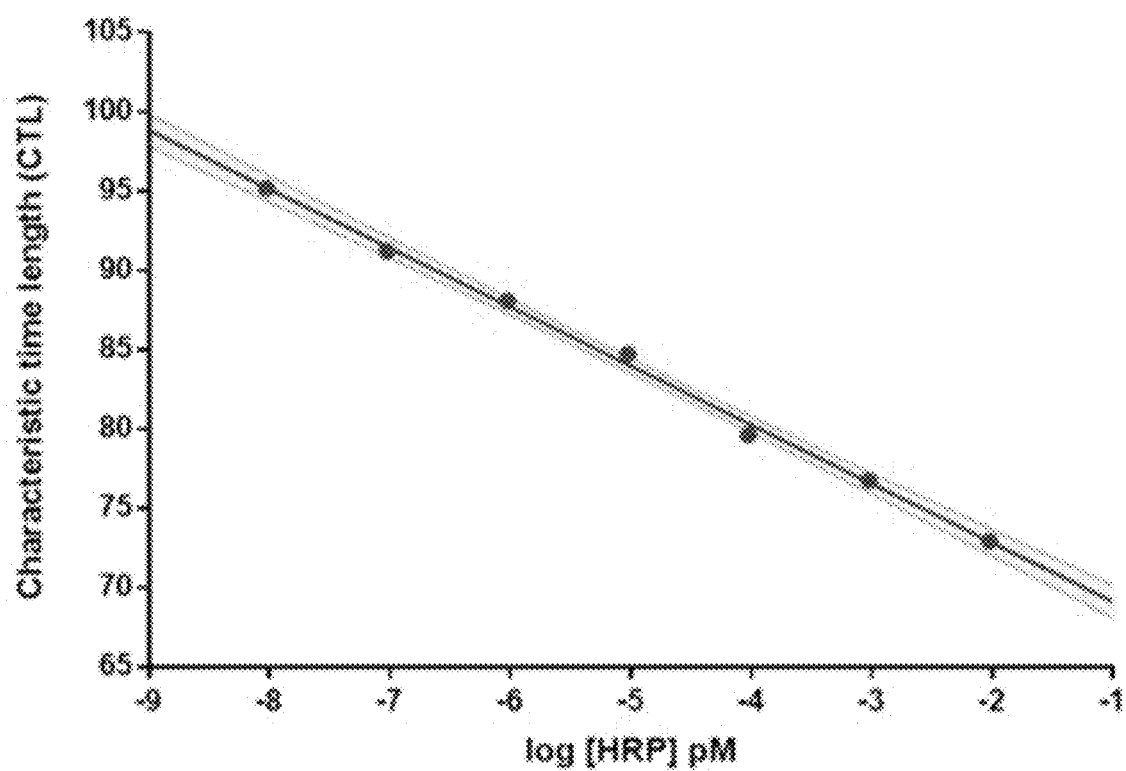
FIG. 7 is a graph showing CTL (characteristic time length) index extraction values of the photo-oxidation induced amplification pattern depending on the concentration of the enzyme labeled on the antibody according to Example 1 of the present invention.

Further, FIG. 7 is a graph showing CTL (characteristic time length) index extraction values of the photo-oxidation induced amplification pattern depending on the concentration of the enzyme labeled on the antibody according to Example 1 of the present invention. As can be seen in FIG. 7, as the concentration of the enzyme is reduced, the CTL index of the photo-oxidation induced amplification pattern is increased. Accordingly, the concentration of the enzyme at a low concentration or in a small amount may be more accurately quantified with high sensitivity.

Example 2

Next, in Example 2 of the present invention, a photo-oxidation induced amplification pattern is indexed depending on the concentration of a biomarker, thus quantifying the concentration of the biomarker with high sensitivity.

First, samples including various concentrations of biomarkers are prepared, and the biomarker is selectively detected using an antibody, an aptamer, or a nucleic acid specific to the biomarker. As the biomarker, any one may be selected from among a protein, a peptide, a gene, a hormone, and a low-molecular compound. In order to quantify the amount of the biomarker that is detected, a conventional enzyme immunoassay method may be used, in which an antibody, an aptamer, or a nucleic acid specific to a biomarker is labeled with an enzyme.

In Example 2 of the present invention, for example, various concentrations of samples including PSA (prostate specific antigen), which is a kind of protein biomarker, are prepared, and an antibody specific to PSA labeled with an HRP enzyme is used, thus performing the conventional enzyme immunoassay method.

Next, various concentrations of samples including PSA-antibody-HRP complexes are mixed with an Amplex Red substrate to thus perform an enzyme-substrate reaction for a predetermined time, followed by a photo-oxidation induced amplification process according to the same procedure as in Example 1. Accordingly, the description of Example 1 will cover for the measurement of the photo-oxidation induced amplification process and the indexing process of the photo-oxidation induced amplification pattern in Example 2.

Figure 8:
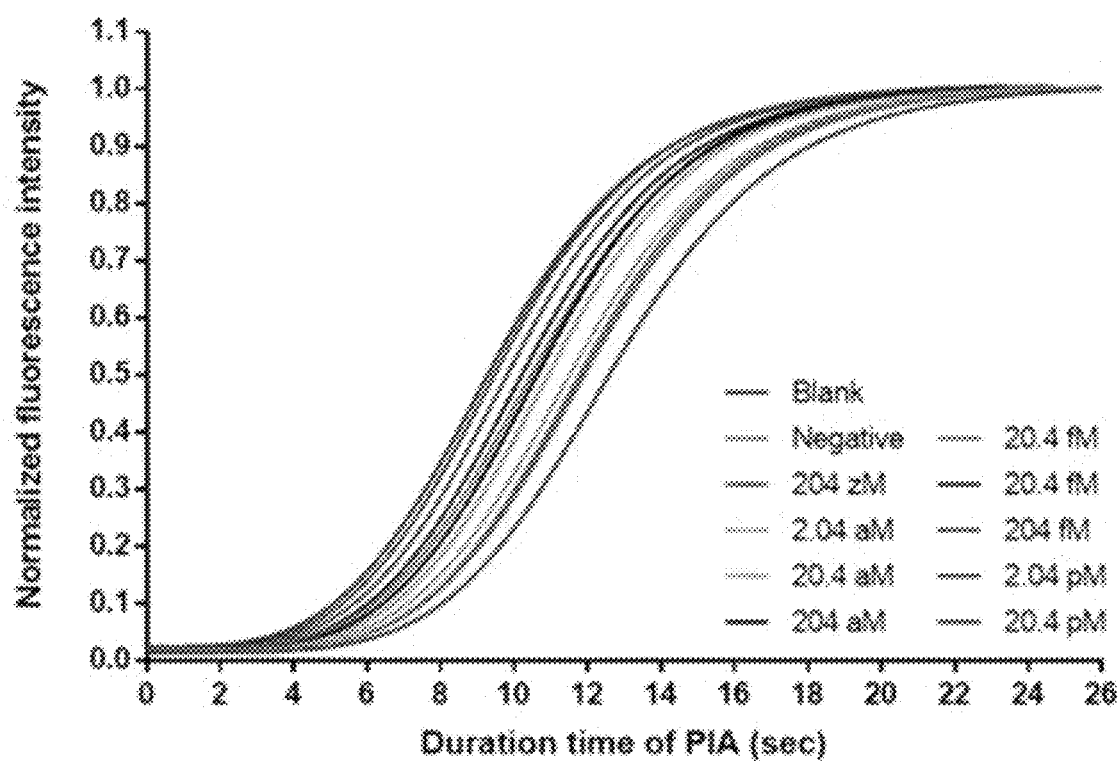
FIG. 8 is a graph showing a photo-oxidation induced amplification pattern over time depending on the concentration of a protein biomarker according to Example 2 of the present invention.
Figure 9:
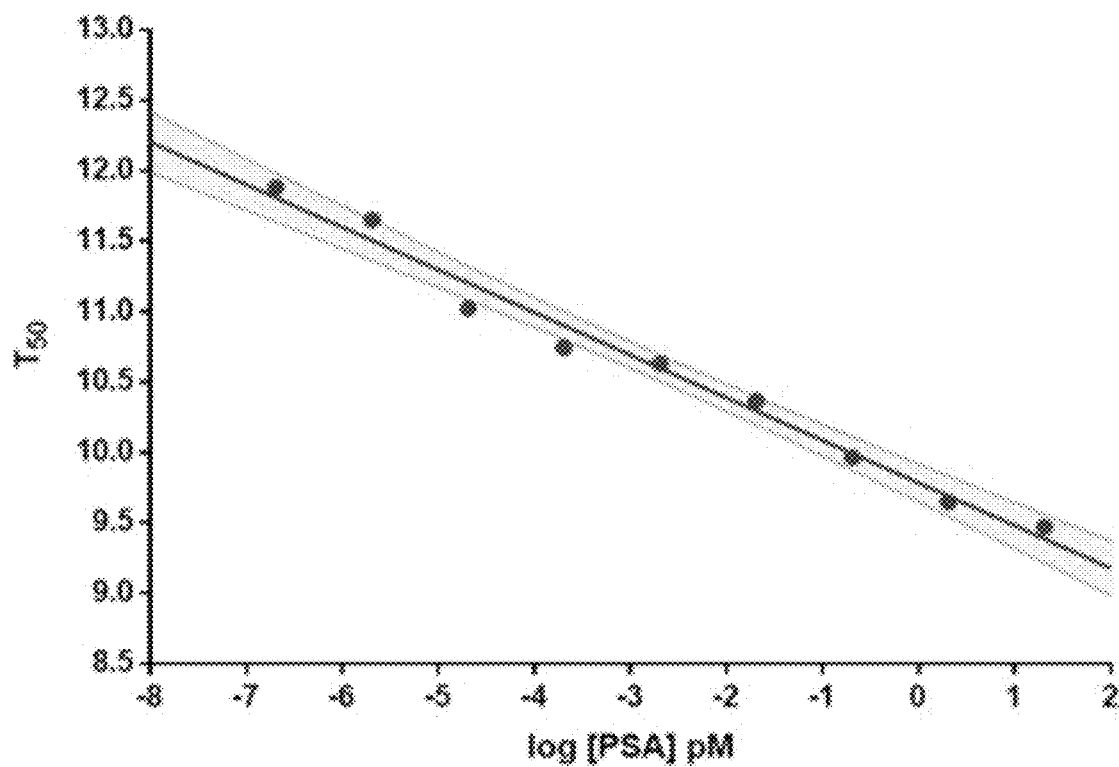
FIG. 9 is a graph showing $T_{50}$ index extraction values of the photo-oxidation induced amplification pattern depending on the concentration of the protein biomarker according to Example 2 of the present invention.
Figure 10:
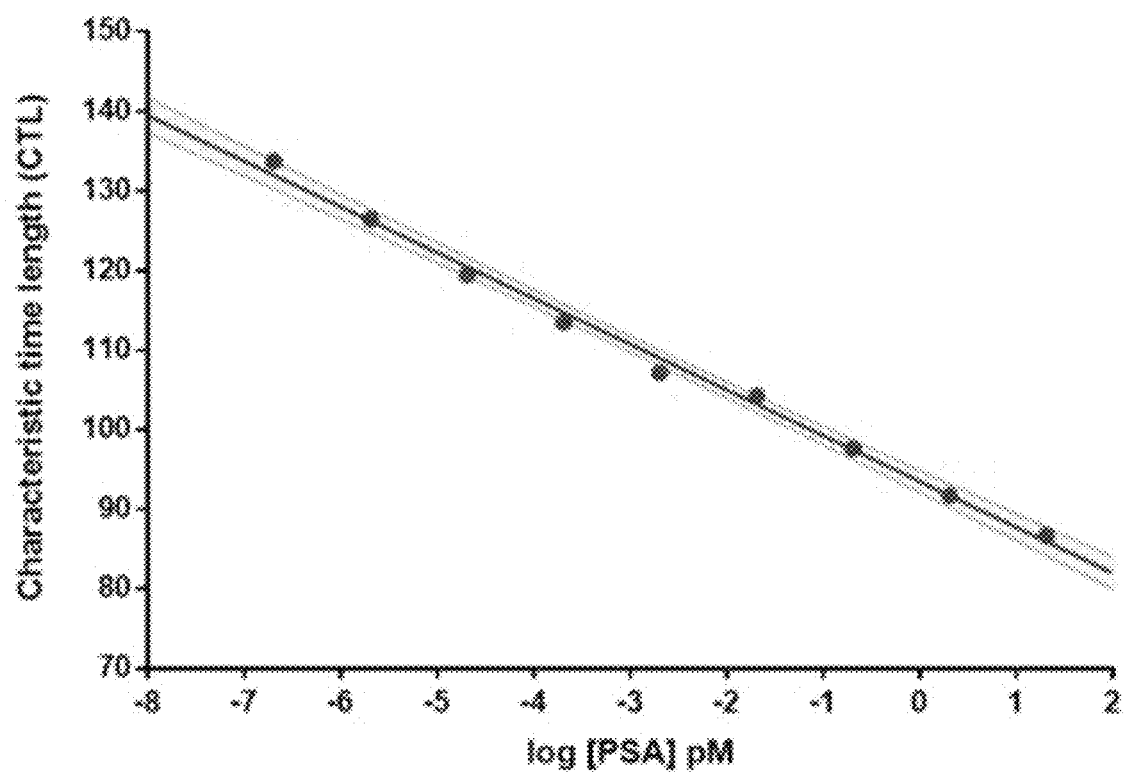
FIG. 10 is a graph showing CTL index extraction values of the photo-oxidation induced amplification pattern depending on the concentration of the protein biomarker according to Example 2 of the present invention.

FIG. 8 is a graph showing a photo-oxidation induced amplification pattern over time, depending on the concentration of a protein biomarker according to Example 2 of the present invention. FIGS. 9 and 10 are graphs showing $T_{50}$ index extraction values of the photo-oxidation induced amplification pattern and CTL index extraction values of the photo-oxidation induced amplification pattern, respectively, depending on the concentration of the protein biomarker.

As shown in FIGS. 8 to 10, in the enzyme immunoassay method using various concentrations of samples including PSA, when the product resulting from the enzyme-substrate reaction is continuously exposed to light to thus perform the photo-oxidation induced amplification, as the concentration of PSA is reduced, a $T_{50}$ index, indicating the time required to reach half of the maximum value of the amount of color formation, light emission, or fluorescence of the product, and a CTL index are increased. Accordingly, the concentration of PSA at a low concentration or in a small amount may be more accurately quantified with high sensitivity. That is, the $T_{50}$ index or the CTL index of the sample including PSA, whose concentration is not known, may be compared to the $T_{50}$ index or the CTL index depending on the concentration of a reference sample including PSA diluted at a predetermined concentration interval, whereby the concentration of PSA included in the measurement sample is more accurately quantified with high sensitivity.

As another example of Example 2 of the present invention, various concentrations of samples including $A\beta_{42}$ (amyloid beta 42), which is a kind of peptide biomarker, are prepared, and an antibody specific to $A\beta_{42}$ labeled with an HRP enzyme is used, thus performing a conventional enzyme immunoassay method.

Next, various concentrations of samples including $A\beta_{42}$-antibody-HRP complexes are mixed with an Amplex Red substrate to thus perform an enzyme-substrate reaction for a predetermined time, followed by a photo-oxidation induced amplification process according to the same procedure as in Example 1. Accordingly, the description of Example 1 will cover for the measurement of the photo-oxidation induced amplification process and the indexing process of the photo-oxidation induced amplification pattern in another example of Example 2.

Figure 11:
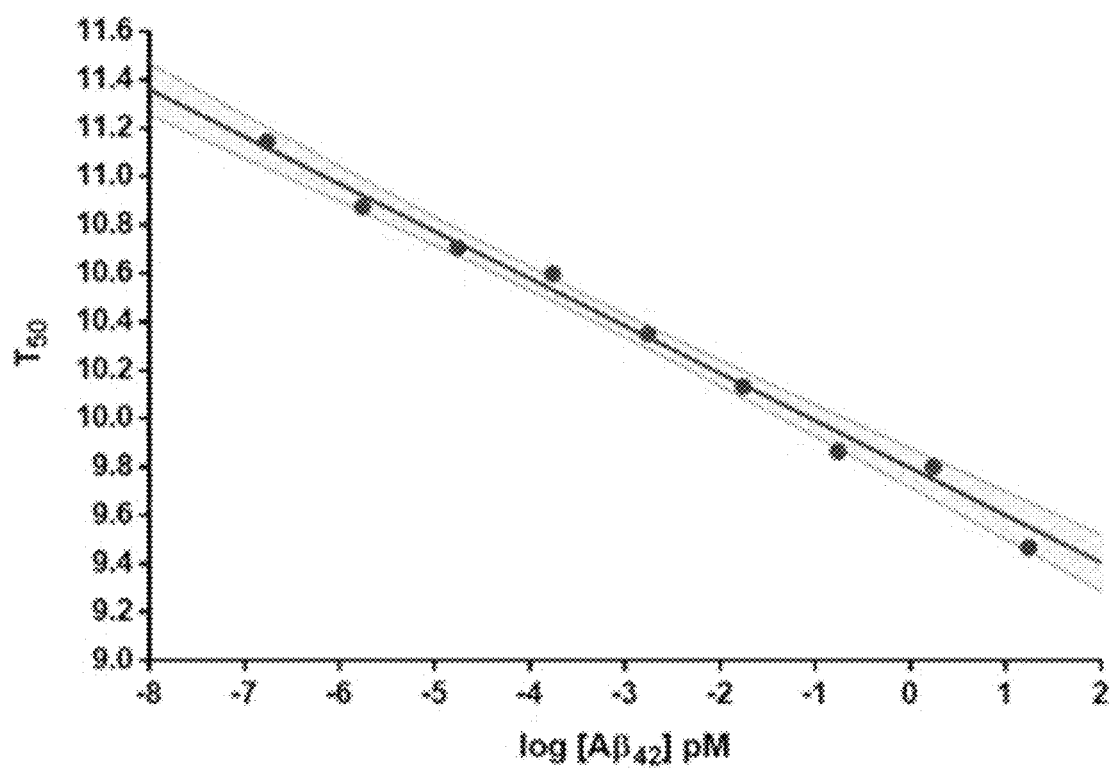
FIG. 11 is a graph showing $T_{50}$ index extraction values of a photo-oxidation induced amplification pattern depending on the concentration of a peptide biomarker according to another example of Example 2 of the present invention.
Figure 12:
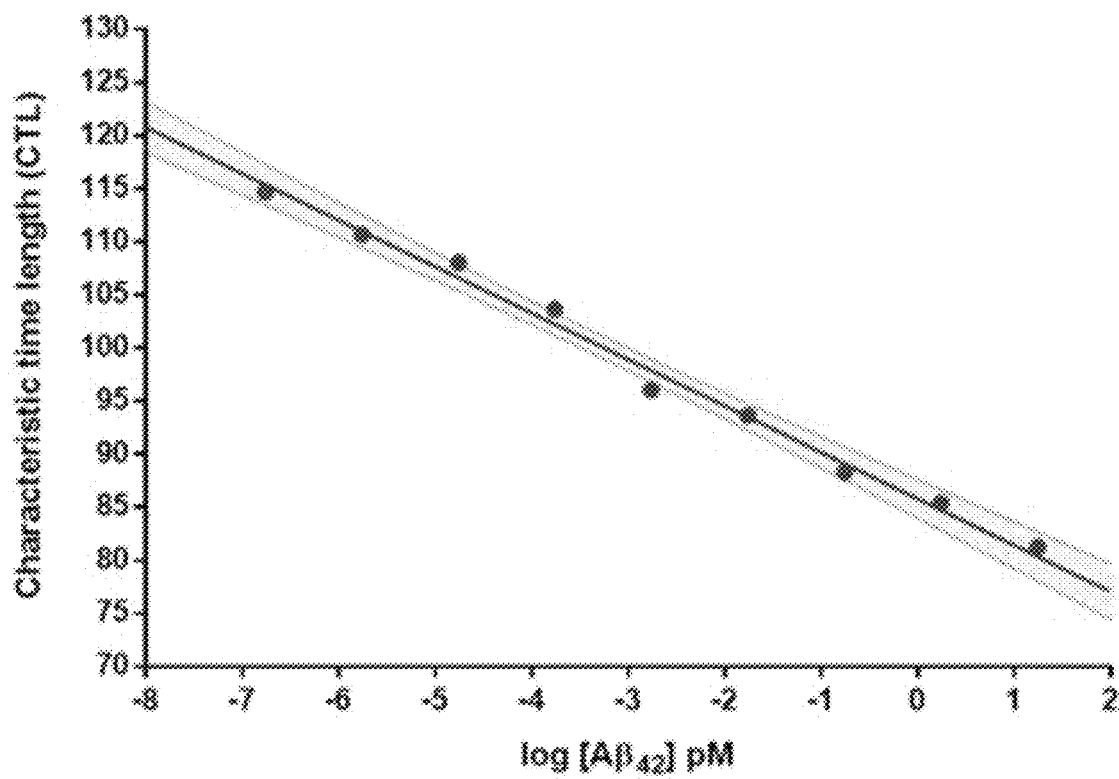
FIG. 12 is a graph showing CTL index extraction values of the photo-oxidation induced amplification pattern depending on the concentration of the peptide biomarker according to another example of Example 2 of the present invention.

FIG. 11 is a graph showing $T_{50}$ index extraction values of a photo-oxidation induced amplification pattern, depending on the concentration of a peptide biomarker according to another example of Example 2 of the present invention. FIG. 12 is a graph showing CTL index extraction values of the photo-oxidation induced amplification pattern depending on the concentration of the peptide biomarker.

As shown in FIGS. 11 and 12, in the enzyme immunoassay method using various concentrations of samples including $A\beta_{42}$, when the product resulting from the enzyme-substrate reaction is continuously exposed to light to thus perform the photo-oxidation induced amplification, as the concentration of $A\beta_{42}$ is reduced, a $T_{50}$ index, indicating the time required to reach half of the maximum value of the amount of color formation, light emission, or fluorescence of the product, and a CTL index are increased. Accordingly, the concentration of $A\beta_{42}$ at a low concentration or in a small amount may be more accurately quantified with high sensitivity. That is, the $T_{50}$ index or the CTL index of the sample including $A\beta_{42}$, whose concentration is not known, may be compared to the $T_{50}$ index or the CTL index depending on the concentration of a reference sample including $A\beta_{42}$ diluted at a predetermined concentration interval, whereby the concentration of $A\beta_{42}$ included in the measurement sample is more accurately quantified with high sensitivity.

INDUSTRIAL APPLICABILITY

As described above, in the present invention, the concentration of a biomarker to be detected may be more accurately quantified with high sensitivity by using various types of biomarkers, various types of antibodies, aptamers, or nucleic acids specifically bound to the biomarkers, various types of enzymes, various types of substrates, and various types of indexes of photo-oxidation induced amplification patterns according to various embodiments.

That is, the type of the antibody, the aptamer, or the nucleic acid may be changed depending on the type of the biomarker to be detected, thus indexing the photo-oxidation induced amplification pattern in the same manner as in Example 2. The resultant index may be compared to an index of a photo-oxidation induced amplification pattern of a reference sample, thereby more accurately quantifying the concentration of the biomarker, which is included at a low concentration or in a small amount in a measurement sample, with high sensitivity.

In a method of quantifying a biomarker with high sensitivity using photo-oxidation induced amplification according to the present invention, a product resulting from a reaction of an enzyme labeled on an antibody, an aptamer, or a nucleic acid, which is specific to the biomarker to be detected, with a substrate is continuously exposed to light, thus performing a photo-oxidation induced amplification process. Further, a variation pattern of amounts of color formation, light emission, and fluorescence of the product is indexed, depending on a photo-oxidation induced amplification time, followed by comparison with the index of the reference sample, whereby a biomarker present at a low concentration or in a small amount may be more accurately quantified with high sensitivity.

Although a preferred embodiment of the present invention has been described for illustrative purposes, it will apparent to those skilled in the art that various changes and modifications can be made within the scope of the present invention as set forth in the appended claims.

The invention claimed is:

1. A method of quantifying a biomarker with high sensitivity using photo-oxidation induced amplification, the method comprising:
   performing an enzyme-substrate reaction of a measurement sample including an enzyme labeled on any one selected from among an antibody, an aptamer, and a nucleic acid which are specifically bound to the biomarker;
   optically measuring one or more optical properties selected from among amounts of color formation, light emission, and fluorescence of a product during a photo-oxidation induced amplification process while the product resulting from the enzyme-substrate reaction is continuously exposed to a light to thus perform the photo-oxidation induced amplification process, wherein the optically measuring step comprises a step of obtaining a time-varying pattern and the time-varying pattern is intensity variation of the measured optical properties obtained as a function of duration time;
   performing a regression analysis with respect to the time-varying pattern and thereby extracting an index of the time-varying pattern using a regression analysis parameter, wherein the regression analysis parameter is selected from the group consisting of a parameter of an optical property initial value, a parameter of an optical property maximum value, a parameter of a time required to reach a half of the optical property maximum value, a parameter of an amplification ratio of the optical properties over time, and combination thereof; and comparing the index to an index of a reference sample containing a predetermined dilution of the biomarker to determine a concentration of the biomarker included in the measurement sample.

2. The method of claim 1, wherein the biomarker includes any one selected from among a protein, a peptide, a gene, a hormone, and a low-molecular compound.

3. The method of claim 1, wherein in the optically measuring the optical properties, the light used during the photo-oxidation induced amplification includes any one selected from among a white light, a monochromatic light, and a laser.

4. The method of claim 1, wherein the optically measuring the optical properties includes continuously measuring the optical properties of the product over time while the product of the enzyme-substrate reaction is continuously exposed to the light.

5. The method of claim 1, wherein the index of the reference sample is the index of the photo-oxidation induced amplification pattern of the reference sample including the biomarker diluted at a predetermined concentration interval.

6. The method of claim 1, wherein the performing the enzyme-substrate reaction of the measurement sample includes mixing the measurement sample, wherein the measurement sample is selected from among peroxidase, galactosidase, and phosphatase, and is labeled on any one selected from among the antibody, the aptamer, and the nucleic acid, with any one substrate selected from among ADHP (10-acetyl-3,7-dihydroxyphenoxazine; Amplex Red), RGP (resorufin-$\beta$-D-galactopyranoside), and MUP (4-methylumbelliferyl phosphate), thus performing the enzyme-substrate reaction for a predetermined time.

7. The method of claim 1, wherein the regression analysis parameter is selected from the group consisting of an optical property initial value, an optical property maximum value, an amplification ratio of the optical properties over time, and combination thereof.

8. The method of claim 1, the method further comprising a step of performing a regression analysis with respect to the reference sample and thereby extracting the index of the reference sample using the regression analysis parameter before the step of performing the enzyme-substrate reaction of the measurement sample.

* * * * *